United States Patent [19]
Pu

[11] Patent Number: 5,484,086
[45] Date of Patent: Jan. 16, 1996

[54] PERFUME GAS GENERATING DEVICE

[76] Inventor: Kuan H. Pu, No. #25 Alley 2 Lane 220 An-Ping Rd., Tainan, Taiwan

[21] Appl. No.: 221,737

[22] Filed: Apr. 1, 1994

[30] Foreign Application Priority Data

Apr. 20, 1993 [CN] China .................. 93210429.0

[51] Int. Cl.⁶ ............................................. B67D 3/00
[52] U.S. Cl. ........................ 222/187; 392/395; 392/406
[58] Field of Search ........................... 222/146.5, 187; 392/394, 395, 403, 406

[56] References Cited

U.S. PATENT DOCUMENTS

| | | | |
|---|---|---|---|
| 2,472,992 | 6/1949 | Szekely | 392/395 X |
| 4,574,181 | 3/1986 | Spector | 392/395 X |
| 4,669,637 | 6/1987 | Fiocco | 222/187 |
| 4,686,353 | 8/1987 | Spector | 392/395 X |
| 4,692,590 | 9/1987 | Spector | 392/395 X |
| 4,937,431 | 6/1990 | Jameson et al. | 392/395 |
| 5,038,394 | 8/1991 | Hasegawa et al. | 392/395 |
| 5,161,646 | 11/1992 | Aurich et al. | 222/187 |
| 5,222,186 | 6/1993 | Schimanski et al. | 392/395 |
| 5,290,546 | 3/1994 | Hasegawa et al. | 392/395 X |

FOREIGN PATENT DOCUMENTS

| | | | |
|---|---|---|---|
| 726101 | 5/1932 | France | 392/395 |
| 62784 | 4/1984 | Japan | 392/395 |
| 45986 | 3/1987 | Japan | 392/395 |
| 337992 | 6/1959 | Taiwan | 392/395 |
| 672097 | 5/1952 | United Kingdom | 392/395 |

*Primary Examiner*—Andres Kashnikow
*Assistant Examiner*—Kenneth R. DeRosa
*Attorney, Agent, or Firm*—Pro-Techtor International

[57] ABSTRACT

A perfume gas generating device including a container for containing the perfume, a cap member associated with a neck portion of the container and formed with at least one opening, a fiber-made wick member disposed in the container and serving as an upward moving path of the perfume in the container, and a heating system including a heating mechanism disposed above the wick member and contacting a top surface thereof, whereby the heating mechanism forms a high temperature area above the top surface of the wick member and the perfume is able to move upward along the wick member into the high temperature area to be vaporized into gas which dissipates to ambient environment.

10 Claims, 4 Drawing Sheets

ര5,484,086

PERFUME GAS GENERATING DEVICE

BACKGROUND OF THE INVENTION

The present invention relates to a gas generating device, and more particularly to a device which forms a high temperature area above a predetermined surface of a perfume for creating gas and dissipating the same to ambient environment.

It is known that an odor agent or odor plate is widely used in a car or a room for creating desired odor. The odor plate is heated by an odor generating device to dissipate gas to the ambient environment. Such device includes a seat portion for placing the odor plate thereon. The seat portion, has a power socket and an interior mace for receiving a heating plate or a resistor. In general, the heating plate or resistor can conduct the heat to the odor plate for creating gas. Naturally, the power source can be a cigarette lighter of a car.

It is known that in using the odor plate, the density of the gas dissipated from the odor plate is unstable. For example, in the preliminary stage of use, the odor plate will release high density gas to create heavy odor. Subsequently, the density of the released gas will apparently decrease and the smell will be unsatisfactory. This is because that the perfume molecules are mostly accumulated on the surface of the odor plate. In more detail, the odor plate is made of a certain thickness of filter board or laminated board which goes through perfume immersion, freezing and drying procedures. In the perfume immersion procedure, the perfume such filtrates into the filter board that the density of the perfume in the surface layer, inner layer and central layer of the filter board is sequentially decreased. Therefore, strictly speaking, the using life of the odor plate is short because that most of the perfume content is released in the preliminary stage of use.

An improved perfume gas generating device is developed to solve the above problem of uneven density of the released gas. Such device includes a base having a power socket and a heating mechanism disposed in the base. Usually, the heating mechanism includes a heating plate member. In such device, a container containing the perfume is allowed to be placed on a table of the base for receiving the heat conducted from the heating mechanism. Therefore, the thinner the table is, the better the heating effect is. In another type of generating device, the perfume is wrapped in a bag member formed with multiple holes, whereby when the perfume is heated, the perfume gas is able to escape through the holes.

Generally, the perfume container of such device is totally heated by the heating mechanism and when not used, the power circuit is open. Accordingly, the whole bottle or bag of perfume is alternately put under a hot using state and a cold not using state. This causes consumption of more thermal energy and deterioration of the quality of the perfume.

Therefore, it is necessary to develop a perfume gas generating device which does not heat the whole perfume contained in the container at the same time and releases perfume gas at even density.

SUMMARY OF THE INVENTION

It is a primary object of the present invention to provide an improved perfume gas generating device in which the whole perfume is not alternately heated and cooled so that the quality of the perfume remains satisfactory and the consumption of heat is lower than a conventional device. Also, the density of released gas is kept constant. Particularly, the perfume gas generating device of the present invention includes a container for containing the perfume. The container has a cap member formed with at least one opening. A fiber-made wick member is placed in the container with a certain length of the wick extending through the opening of the cap and protruding beyond the cap for contacting with a heating system. The heating system includes a heating mechanism disposed above the cap and a heat source controlling circuit for conducting heat to the heating mechanism. Substantially, the heating mechanism forms a high temperature area on the contacting surface of the wick member, whereby the perfume contained in the container can gradually ascend along the wick up to the contacting surface in the high temperature area to vaporize into perfume gas which is dissipated to ambient environment. Because the heating system forms the high temperature area only on the top contacting surface of the wick, the whole bottle or bag of perfume is prevented from being alternately heated and cooled and thus the quality of the perfume is prevented from being deteriorated.

The heat source controlling circuit of the heating system includes at least an oscillating circuit, a transistor and a diode for controlling the heating frequency of the heating mechanism. In fact, the heating system only provides heat for the perfume reaching the top contacting surface of the wick member. Therefore, the heat consumption of the present invention is lower than the conventional device which heats the whole bottle or bag of perfume.

The present invention can be best understood through the following description and accompanying drawing, wherein:

DETAILED DESCRIPTION OF THE PREFERRED EMBODIMENTS

Figure 1:
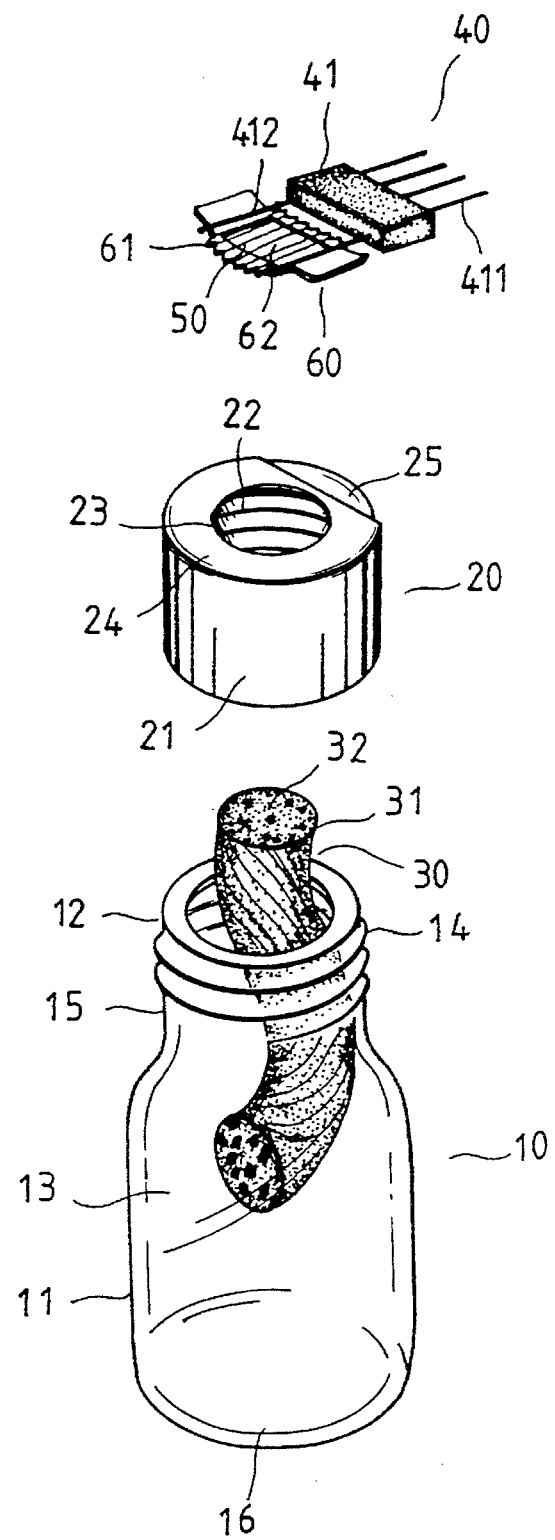
FIG. 1 is a perspective exploded view of the present invention.
Figure 2:
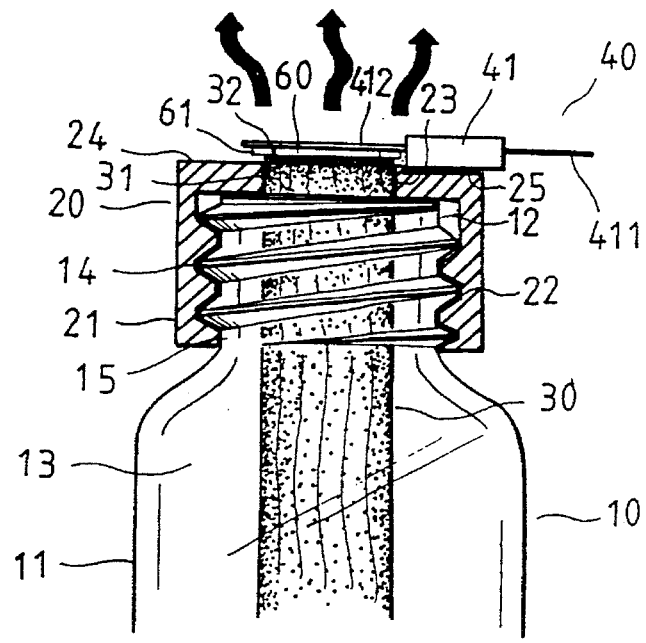
FIG. 2 is a sectional assembled view of a part of the present invention, showing that the top surface of the wick member contacts with the heating mechanism.

Please refer to FIGS. 1 and 2. The perfume gas generating device of the present invention includes a container 10 having a main body 11, a neck portion 12 formed on an upper end of the main body 11, and a reservoir 13 defined by the main body 11 for containing a perfume solvent or the like. The container 10 is preferably a glass bottle which is easily available and is more suitable for storing the perfume solvent. An outer thread portion 14 is formed on the periphery 15 of the neck 12 for screwing a cap member 20 thereon. The cap member 20 has a peripheral wall 21 and an end wall 24. An inner thread portion 22 is formed on inner side of the peripheral wall 21 corresponding to the outer thread portion 14. The cap member 20 further has an opening 23 for communicating the reservoir 13 with the ambient environment.

In the preferred embodiment of the present invention, a fiber-made wick member 30 is disposed in the container 10. The wick member 30 extends from a bottom end 16 of the container 10 to the opening 23 of the cap 20, serving as a filtrating and moving (capillarity) path of the perfume in the reservoir 13. The length of the wick member 30 is slightly greater than the distance between the bottom end 16 of the container 10 and the end wall 24 of the cap 20 so that a top end 31 of the wick member 30 slightly protrudes above the opening 22 of the cap member 20 for receiving the heat conducted from the heating system 40. Detailedly speaking, the heating system 40 at least includes a heating mechanism 41 having a heat input end 411 and a heat output end 412, and a heat source controlling circuit 42 for conducting heat to the heating mechanism 41 (as shown in FIG. 4). The end wall 24 of the cap member 20 is formed with a recess portion 25, permitting the heating mechanism 41 to be affixed on the cap member 20 by adhesive or other measures. The recess portion 25 is such located that after fixing the heating mechanism 41, the heat output end 412 bridges over the opening 23 of the cap member 20 as shown in FIG. 3.

Several loops of heating wire 50 is wound on the heat output end 412 of the heating mechanism 41 to contact with a top contacting surface 32 of the wick member 30. After entering the heating mechanism 41, the heat is conducted from the heat output end 412 to the heating wire 50 to form a high temperature area above the contacting surface 32 of the wick member 30 so as to vaporize the perfume solvent reaching the contacting surface 32 by capillarity. Preferably, a support member 60 is disposed between the heat output end 412 and the cap 20, whereby the heating wire 50 can be wound on two lateral tooth ends 61 of the support member 60. Usually, the support member 60 further includes a hollow section 62, whereby the top end 31 of the wick member 30 can extend through the opening 23 of the cap member 20 and the hollow section 62 to contact with the heating wire 50.

Please refer to FIG. 4. The heat source controlling circuit 42 of the heating system includes a transistor 422, a current-limiting resistor 424, a diode 425 and an oscillating circuit 423 having a variable resistor 426. The input end 411 of the heating mechanism 41 is connected with a power source end 421 and the collector of the transistor 422. Also, the oscillating circuit 423 is connected with the base of the transistor 422 through the current-limiting resistor 424 and the diode 425 for controlling the heating frequency of the heating wire 50 of the heating mechanism 41. The oscillating circuit 423 is used for creating oscillating signal and the variable resistor 426 controls the oscillating frequency. By means of the current-limiting resistor 424 and the diode 425 for half-wave rectification, the oscillating signal is limited to positive half-wave for biasing the base of the transistor 422 and creating a current ice for heating the heating mechanism 41. Therefore, the higher the frequency is, the higher the temperature maintained by the heating mechanism 41 is so as to achieve the temperature controlling effect and thus control the vaporizing speed of various kinds of perfumes with different vaporizing temperatures.

Figure 3:
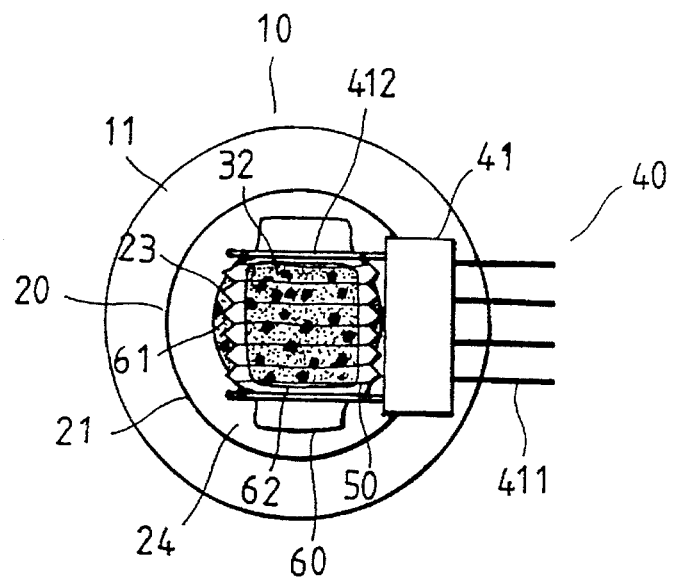
FIG. 3 is a top view according to FIG. 2, showing that the heat output end of the heating mechanism is disposed above the top surface of the wick member.
Figure 4:
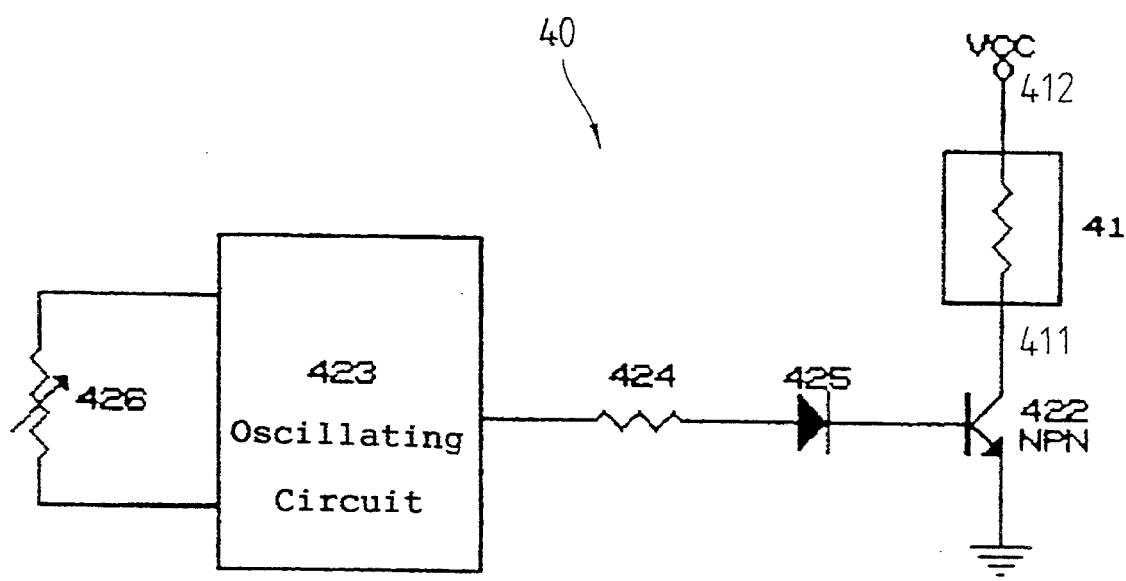
FIG. 4 is a circuit diagram of the heating system of the present invention.

Please further refer to FIGS. 2 and 3. The perfume contained in the reservoir 13 by capillarity is taken up to the contacting surface 32 along the wick member 30 into the high temperature area formed by the heating wire 50 of the heating mechanism 41. The perfume solvent on the contacting surface 32 is quickly vaporized into gas which dissipates to the ambient environment. Because the high temperature area is limited on the contacting surface 32 of the wick member 30, the perfume is prevented from being totally alternately heated and cooled and the deterioration of the quality of the perfume is avoided. Also, because the heating system 40 only provides heat for the perfume reaching the contacting surface 32, the heat consumption is lower than the conventional device which heats the entire perfume. It should be noted that the resistance of the perfume is 3.9 MK$\Omega$ high so that a short circuit will not occur due to the contact between the heating wire 50 with 10–200$\Omega$ resistance and the wetted wick member 30.

Figure 5:
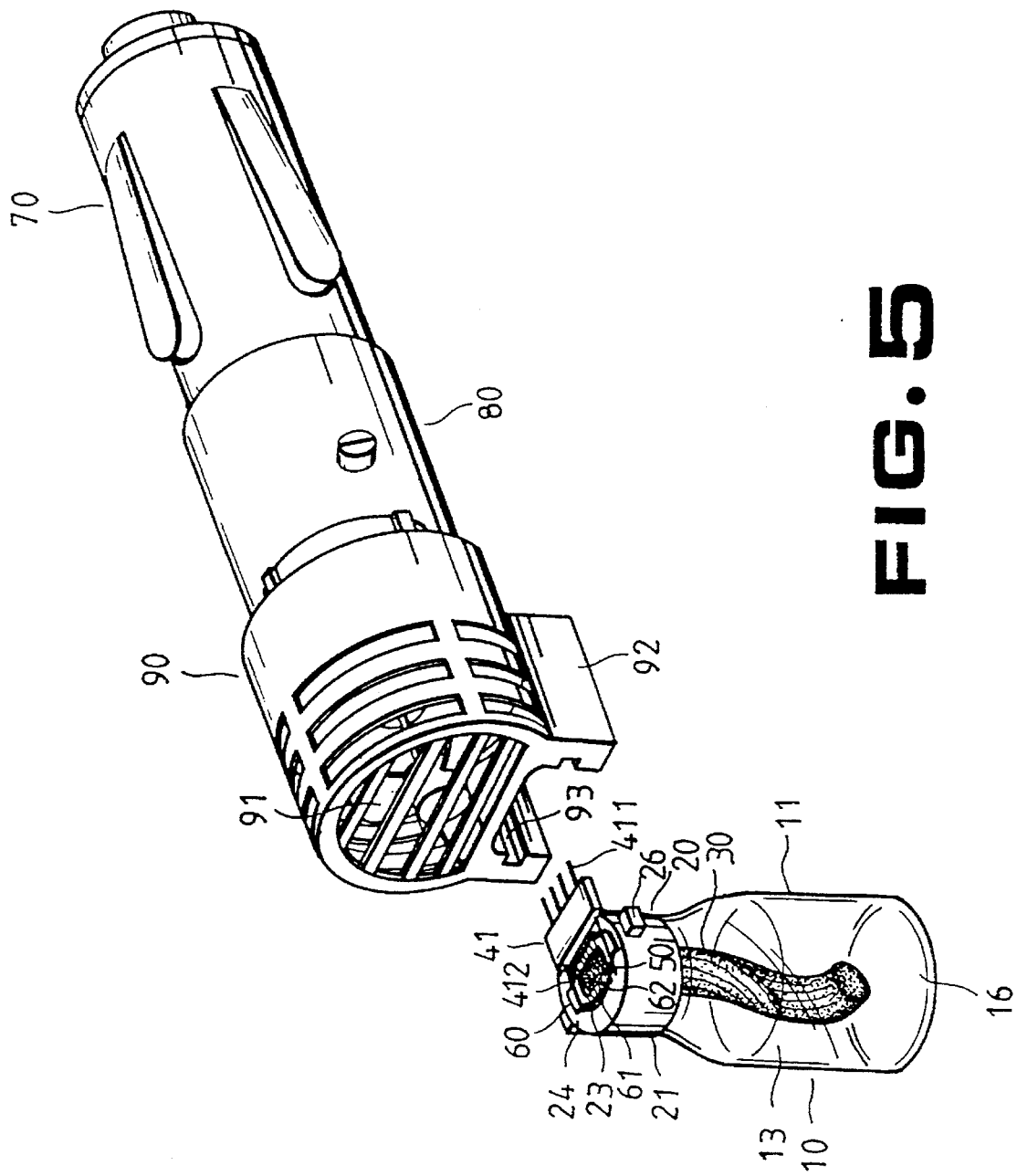
FIG. 5 shows another embodiment of the present invention, wherein the power source is replaced by a cigarette lighter which has a base for fitting with the perfume gas generating device of the present invention.

Please refer to FIG. 5. In another embodiment of the present invention, a base member 80 is disposed at a front end of a cigarette lighter 70. The base member 80 is slidably fitted with a head body 90 having a fan 91. Preferably, a connecting seat 92 having rails 93 is disposed under the head body 90 for connecting with the perfume gas generating device 100. In this embodiment, the cap member 20 is formed with two slide blocks 26 on the peripheral wall 21 corresponding to the rails 93 of the connecting seat 92, whereby the perfume gas generating device 100 is able to fit into the connecting seat 92 with the slide blocks 26 sliding along the rails 93. After the device 100 is fitted into the connecting seat 92, the heat input end 411 of the heating mechanism 41 can be inserted into a connecting terminal (not shown) disposed at a rear end of the connecting seat 92 to electrically connect therewith. Therefore, the cigarette lighter 70 serves as a power source for the heating mechanism 41.

According to the above, the present invention provides an effective perfume gas generating device in which the whole perfume is not alternately heated and cooled so that the quality of the perfume remains satisfactory and the consumption of heat is lower than a conventional device. Also, the density of released gas is kept constant.

It is to be understood that the above description and drawings are only used for illustrating one embodiment of the present invention, not intended to limit the scope thereof. Any variation and derivation from the above description and drawings should be included in the scope of the present invention.

What is claimed is:

1. A perfume gas generating device including:
   a container for containing the perfume, said container having a main body, a neck portion formed on an upper end of said main body, and a reservoir defined by said main body;
   a cap member associated with said neck portion of said container, having at least one opening;
   a fiber-made wick member disposed in said reservoir of said container, said wick member serving as an upward moving path of the perfume in said reservoir and having a top end extending outside said neck portion of said container; and
   a heating system including a heating mechanism disposed above said wick member, having a heat input end and a heat output end, and a heat source controlling circuit for conducting heat to said heating mechanism, whereby
   said heating mechanism forms a high temperature area above said top end of said wick member and the perfume is able to move upward along said wick member into said high temperature area to be vaporized into gas which dissipates into the ambient environment, said heating mechanism including a transistor connected with said input end of said heating mechanism, a diode and a current-limiting resistor connected with said transistor, and an oscillating circuit having a variable resistor, whereby said oscillating circuit is connected with said transistor through said current-limiting resistor and diode.

2. A perfume gas generating device as claimed in claim 1, wherein said cap member has an end wall formed with a recess portion, permitting said heating mechanism to be disposed thereon.

3. A perfume gas generating device as claimed in claim 1, wherein the length of said wick member is such that said wick member extends from a bottom of said container to said opening of said cap member with said top end of said wick member protruding beyond said opening by a predetermined length to contact with said output end of said heating mechanism.

4. A perfume gas generating device as claimed in claim 1, wherein a heating wire is wound on said output end of said heating mechanism to contact a top surface of said top end of said wick member.

5. A perfume gas generating device as claimed in claim 1, wherein a support member is disposed between said output end of said heating mechanism and said cap member, said support member having a hollow section and two lateral tooth ends, whereby a heating wire is wound on said tooth ends and said top end of said wick member passes through said hollow section to contact with said heating wire.

6. A perfume gas generating device including:

a container for containing the perfume, said container having a main body, a neck portion formed on an upper end of said main body, and a reservoir defined by said main body;

a cap member associated with said neck portion of said container, having at least one opening;

a fiber-made wick member disposed in said reservoir of said container, said wick member serving as an upward moving path of the perfume in said reservoir and having a top end extending outside said neck portion of said container; and a heating system including a heating mechanism disposed above said wick member, having a heat input end and a heat output end, and a heat source controlling circuit for conducting heat to said heating mechanism, whereby said heating mechanism forms a high temperature area above said top end of said wick member and the perfume is able to move upward along said wick member into said high temperature area to be vaporized into gas which dissipates into the ambient environment;

wherein a base member is disposed at a front end of a cigarette lighter, said base member being slidably fitted with a head body, a connecting seat having rails being disposed under said head body for connecting with said perfume gas generating device, said cap member being formed with two slide blocks corresponding to said rails of said connecting seat, whereby said perfume gas generating device is able to fit into said connecting seat with said slide blocks sliding along said rails.

7. A perfume gas generating device as claimed in claim 6 wherein:

said cap member has an end wall formed with a recess portion in which said heating mechanism is disposed.

8. A perfume gas generating device as claimed in claim 6 wherein:

the length of said wick member is such that said wick member extends from a bottom of said container to said opening of said cap member with said top end of said wick member protruding beyond said opening by a predetermined length to contact with said output end of said heating mechanism.

9. A perfume gas generating device as claimed in claim 6 wherein:

a heating wire is wound on said output end of said heating mechanism to contact a top surface of said top end of said wick member.

10. A perfume gas generating device as claimed in claim 6 wherein:

a support member is disposed between said output end of said heating mechanism and said cap member, said support member having a hollow section and two lateral tooth ends, whereby a heating wire is wound on said tooth ends and said top end of said wick member passes through said hollow section to contact said heating wire.

* * * * *